US006284915B2

(12) United States Patent
Hirase et al.

(10) Patent No.: US 6,284,915 B2
(45) Date of Patent: *Sep. 4, 2001

(54) PROCESS FOR PREPARING 2-AMINO MALONIC ACID DERIVATIVES AND 2-AMINO-1,3-PROPANEDIOL DERIVATIVES, AND INTERMEDIATES FOR PREPARING THE SAME

(75) Inventors: Susumu Hirase; Shigeo Sasaki, both of Kobe; Masahiko Yoneta, Hadano; Ryoji Hirose, Kobe; Tetsuro Fujita, Muko, all of (JP)

(73) Assignees: Taito Co., LTD, Tokyo; Welfide Corporation, Osaka, both of (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/261,342

(22) Filed: Mar. 3, 1999

Related U.S. Application Data

(63) Continuation of application No. PCT/JP98/02998, filed on Jul. 3, 1998.

(30) Foreign Application Priority Data

Jul. 3, 1997 (JP) .................................................... 97-2299

(51) Int. Cl.[7] .............................................. C07C 229/28
(52) U.S. Cl. ................................ 560/39; 560/40; 568/31; 568/331; 568/336
(58) Field of Search ................................ 568/336, 331, 568/31; 560/39, 40

(56) References Cited

U.S. PATENT DOCUMENTS

| 3,835,161 | | 9/1974 | De Muylder . |
| 4,035,427 | * | 7/1977 | Nadelson ............................. 560/254 |
| 4,051,261 | | 9/1977 | Anderson et al. . |
| 4,200,466 | | 4/1980 | Fujiwhara et al. . |
| 5,604,229 | * | 2/1997 | Fujita et al. ......................... 514/255 |
| 5,948,820 | * | 9/1999 | Fujita et al. ......................... 514/653 |

FOREIGN PATENT DOCUMENTS

| 284174 | 9/1988 | (EP) . |
| 49-56947 | 6/1974 | (JP) . |
| 52-108943 | 12/1977 | (JP) . |
| 59-84870 | 5/1984 | (JP) . |
| 60-116647 | 6/1985 | (JP) . |
| 61-137835 | 6/1986 | (JP) . |
| 63-216875 | 9/1988 | (JP) . |
| 2-19343 | 1/1990 | (JP) . |
| 2-138276 | 5/1990 | (JP) . |
| 5-4944 | 1/1993 | (JP) . |
| WO 94/08943 | 4/1994 | (WO) . |
| WO 96/06068 | 2/1996 | (WO) . |

OTHER PUBLICATIONS

Chemical Abstracts, vol. 27, No. 17, Apr. 27, 1970, Pogosyan, G.M., et al., "Styrene Derivatives," p. 341, Column 1, XP002154122.

W. Michaelis et al., "The Metabolism of Pyrovalerone Hydrochloride," *Journal of Medicinal Chemistry*, vol. 13, No. 3, 1970, pp. 497–503.

A. Shiozawa et al., "Synthesis and Activity of 2–Methyl–3–Aminopropiophenones as Centrally Acting Muscle Relaxants", *Eur. J. Med. Chem.*, (1995) 30, 85–94.

Joseph I. Degraw et al., "Experimentally Induced Phenylketonuria," *Journal of Medicinal Chemistry*, vol. 11, 1968, pp. 225–227, XP000971008.

Database CAPLUS on STN, Acc. No. 1998:682349, Adachi et al., 'Preparation of 2–aminopropane–1,3–diol compounds as immunosuppressants.' WO 9845249 (abstract), Oct. 15, 199.*

Database CAPLUS on STN, Acc. No. 1968:75369, Theisen et al., 'Experimentally induced phenylketonuria. II. Potential inhibitors of phenylalanine hydroxylase,' J. Med. Chem. (1968), 11(2), pp. 225–227.*

(List continued on next page.)

Primary Examiner—Johann Richter
Assistant Examiner—Brian J. Davis
(74) *Attorney, Agent, or Firm*—Oblon, Spivak, McClelland, Maier & Neustadt, P.C.

(57) ABSTRACT

A process for preparing 2-amino malonic acid derivatives of formula (1):

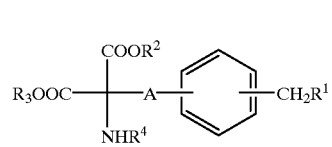

(1)

wherein A is linear or branched chain alkylene having from 1 to 10 carbon atoms, $R^1$ is linear or branched chain alkyl having from 2 to 20 carbon atoms, $R^2$ and $R^3$ are the same or different, and are lower alkyl or aralkyl, and $R^4$ is a protecting group, which process comprises the steps of reducing a compound of formula (6):

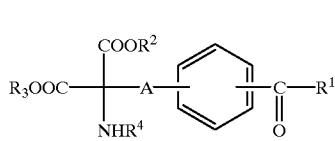

(6)

wherein A is linear or branched chain alkylene having from 1 to 10 carbon atoms, $R^1$ is linear or branched chain alkyl having from 2 to 20 carbon atoms, $R^2$ and $R^3$ are the same or different, and are lower alkyl or aralkyl, and $R^4$ is a protecting group.

47 Claims, 1 Drawing Sheet

OTHER PUBLICATIONS

Database CAPLUS on STN, Acc. No. 1970:89972, Pogosyan et al., 'Styrene derivatives. IX. Synthesis and polymerization of 4–acylstyrenes.' Arm. Khim. Zh. (1969), 22(10), pp. 908–914.*

Hashizume et al, "Synthesis and biological activity of new 3–hydroxy–3–methylglutaryl–CoA synthase inhibitors:2–oxetanones with a meta–sustitituent on the benzene ring in the side chain", Chem. Phar. Bull. 1994, vol. 42, No. 6, pp. 1272–1278, Compound 28.

Sudalai et al, "Studies in terpenoids. LXXXVII, Synthesis of 1,1–dimethyl–7–isobutyryltetralin, and its conversion into 7–tert–butyl–1,1–dimethyltetral in, a rearrangement product of 10–methylenelongibornane", Indian, J. Chem., Sect. B, 1989, vol. 28B, No. 5, pp. 369–371, Compound 8.

Yamamoto et al, "Stero–,chemo–, and regioselective reductions of carbonyl groups via the lithium di–n–butyl–9–borabicyclo [3.3.1]nonane"ate" complex", J. Am. Chem. Soc. 1976, vol. 98, No. 7, pp. 1965–1967, eq5.

Kobayashi et al, Photoinduced molecular transformations. Part 137. New general synthesis of 3–substituted 3,4–dihydro–1H–2–benzopyran–1–ones (3,4–dihydroisocomarines) via radical and photochemical fragementations as the key step, J. Chem. Soc., Perkin Trans. 1, 1993, No. 1, pp. 111–115. Compounds 3' a,3'd.

RES. Inst., et al, "Metabolism of pyrovaleraone hydrochloride", J. Med. Chem. 1970, vol. 13, No. 3, pp. 497–503, Compound 15.

Miller, "Metal–promoted Fries rearrangement", J. Org. Chem. 1987. vol. 52, No. 2, pp. 322–323, Compound 11.

Matsuda et al, "Quantitative structure–activity studies of pyrethroids. 17. Physichochemical substitutent effects of stustituted bynzyl esters of kadethric acid on symptomatic and neurophysiological activities", Pestic. Biochem. Physiol. 1989, vol. 35, No. 3, pp. 300–314, Compounds 27, 28.

Strub–Leconte et al, "Synthesis and photochemical degradation of photocleavable cationic surfactants", Bull. Soc. Chim. Belg 1991, vol. 100, No. 2, pp. 137–144, Table 1.

* cited by examiner

PROCESS FOR PREPARING 2-AMINO MALONIC ACID DERIVATIVES AND 2-AMINO-1,3-PROPANEDIOL DERIVATIVES, AND INTERMEDIATES FOR PREPARING THE SAME

This application is a Continuation of International Application Serial No. PCT/JP98/02998 Filed on Jul. 3, 1998.

TECHNICAL FIELD

The present invention relates to a process for preparing 2-amino malonic acid derivatives, 2-amino-1,3-propanediol derivatives and intermediates for preparing the same, which are used for preparing 2-amino-1,3-propanediol derivatives having excellent pharmacological activity, in particular immune suppression activity, rejection suppression activity, and prevention and therapy of auto immune diseases.

BACKGROUND OF THE INVENTION

Japanese Patent No. 2579602 (U.S. Pat. No. 5,604,229) discloses 2-amino-1,3-propanediol derivatives, and their properties such as pharmacological activity. The patent is herein incorporated by reference in their entirety.

The patent discloses a process for preparing 2-amino-1,3-propanediol derivatives. However, the process has disadvantages in that it contains many complicated steps, and it produces intermediates as oily substances or various isomeric mixtures. Accordingly, it is necessary to isolate and purify the intermediate products by conventional methods such as silica gel chromatography which accompany with complicated operation and use of large quantity of organic solvent. For that reason, it is difficult to remove undesired isomers, homologues, and other impurities. Thus, there is a need to a process which makes it possible to prepare an intended product with high purity, in high yield, without complicated steps, and in a large scale. That is, there is a need to a process which makes it possible to prepare 2-amino malonic acid derivatives and 2-amino-1,3-propandiol derivatives easily in a high yield.

SUMMARY OF THE INVENTION

Accordingly, an object of the present invention is to provide a process for preparing 2-amino malonic acid derivatives and 2-amino-1,3-propanediol derivatives, which permits the production thereof in a high yield readily.

Another object of the present invention is to provide intermediates for preparing 2-amino-1,3-propanediol derivatives.

After intensive investigations, the inventors have found that the above-described objects of the present invention can be attained by preparing 2-amino-1,3-propanediol derivatives and 2-amino malonic acid derivatives via a specific synthetic route.

The present invention has been completed on the basis of the above-described finding. The present invention provides a process for preparing 2-amino malonic acid derivatives of formula (1):

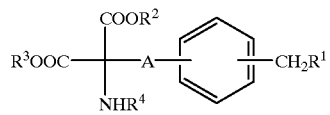

wherein A is linear or branched chain alkylene having from 1 to 10 carbon atoms, $R^1$ is linear or branched chain alkyl having from 2 to 20 carbon atoms, $R^2$ and $R^3$ are the same or different, and are lower alkyl or aralkyl, and $R^4$ is a protecting group, which process comprises the step of reducing a compound of formula (6).

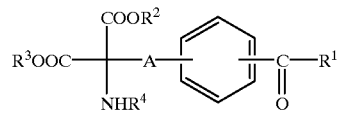

wherein A is linear or branched chain alkylene having from 1 to 10 carbon atoms, $R^1$ is linear or branched chain alkyl having from 2 to 20 carbon atoms, $R^2$ and $R^3$ are the same or different, and are lower alkyl or aralkyl, and $R^4$ is a protecting group.

The present invention also provides a process for preparing the compound of the formula (6), which process comprises the step of reacting a compound of formula (7):

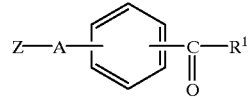

wherein A is linear or branched chain alkylene having from 1 to 10 carbon atoms, $R^1$ is linear or branched chain alkyl having from 2 to 20 carbon atoms, and Z is a leaving group, and 2-(N-substituted)amino malonic diester of formula (3):

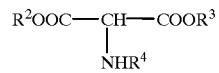

wherein $R^2$ and $R^3$ are the same or different, and are lower alkyl or aralkyl, and $R^4$ is a protecting group.

The present invention also provides a process for preparing 2-amino-1,3-propanediol derivative of formula (17):

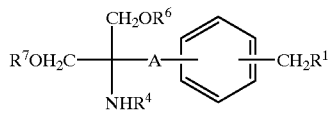

wherein A is linear or branched chain alkylene having from 1 to 10 carbon atoms, $R^1$ is linear or branched chain alkyl having from 2 to 20 carbon atoms, and $R^4$, $R^6$ and $R^7$ are the same or different, and are hydrogen or protecting groups;

which comprises the steps of reducing a compound of formula (19).

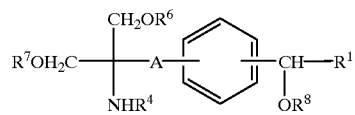

(19)

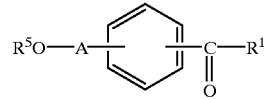

(9)

wherein A is linear or branched chain alkylene having from 1 to 10 carbon atoms, $R^1$ is linear or branched chain alkyl having from 2 to 20 carbon atoms, and $R^4$, $R^6$, $R^7$ and $R^8$ are the same or different, and are hydrogen or protecting groups, and deprotecting the compound obtained in the reducing step.

The present invention also provides intermediates for lo preparing the 2-amino malonic acid derivatives.

BEST MODE FOR CARRYING OUT THE INVENTION

Figure 1:
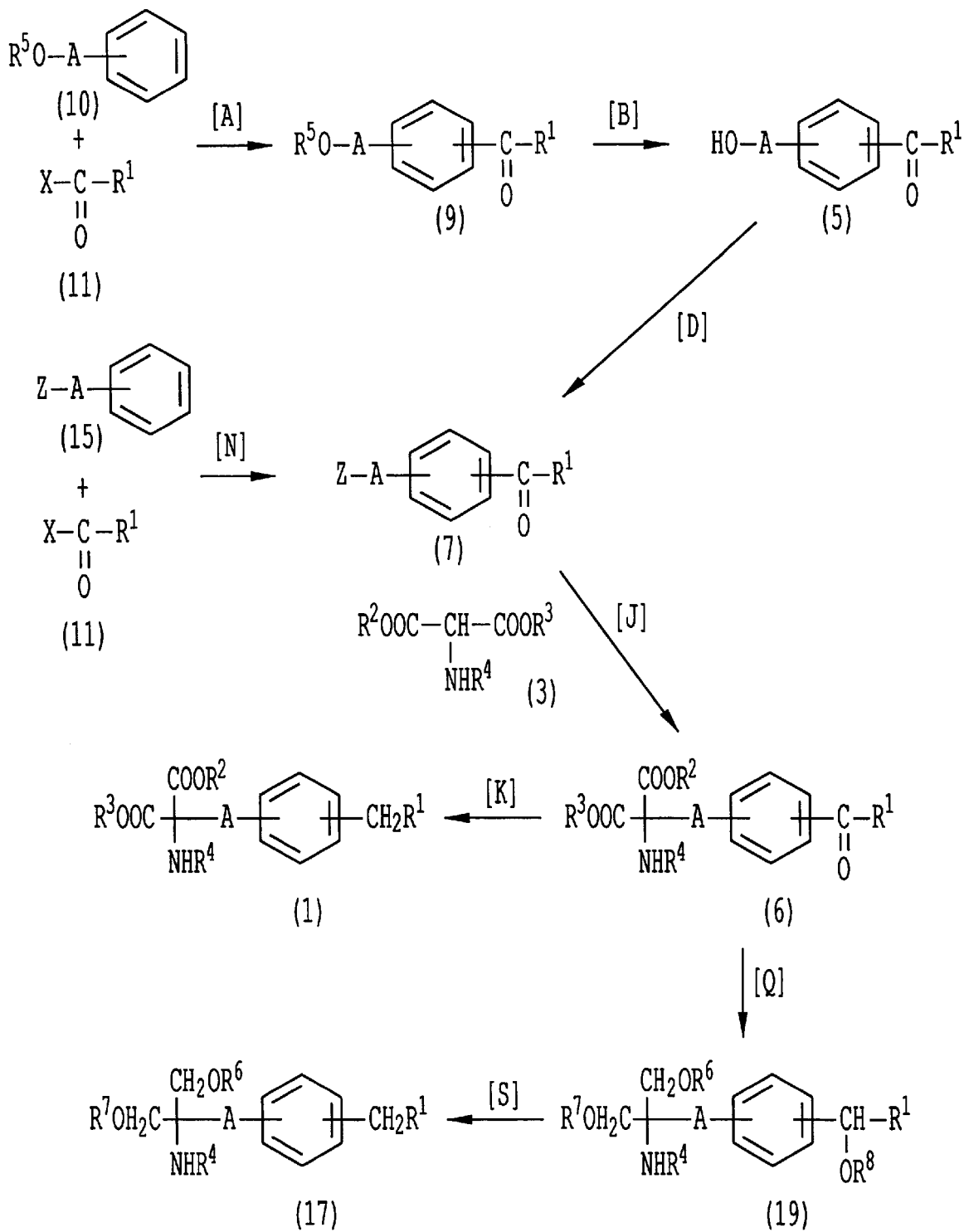
FIG. 1 shows the synthetic route of the process for preparing 2-amino malonic acid derivatives and 2-amino-1,3-propanediol derivatives of the present invention.

First, the detailed description will be made on the process for preparing 2-amino malonic acid derivatives of formula (1), referring to FIG. 1.

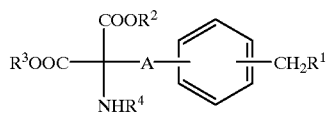

(1)

wherein A is linear or branched chain alkylene having from 1 to 10 carbon atoms, $R^1$ is linear or branched chain alkyl having from 2 to 20 carbon atoms, $R^2$ and $R^3$ are the same or different, and are lower alkyl or aralkyl, and $R^4$ is a protecting group.

A process for preparing 2-amino malonic acid derivatives comprises the following synthetic route, as shown in FIG. 1.

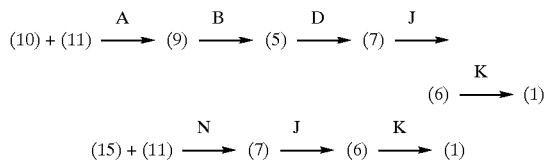

The detailed description will be made on the step A.

In the step A, the compound of formula (9) is prepared by reacting the compound of formula (10) and the compound of formula (11).

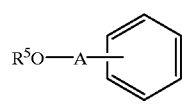

(10)

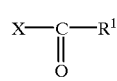

(11)

In the formula (10), A is linear or branched chain alkylene having from 1 to 10 carbon atoms, preferably 1 to 3 carbon atoms, such as methylene, ethylene and propylene. Ethylene is most preferred. $R^5$ is an acyl type protecting group, such as acetyl, benzoyl, trichloroacetyl and pivaloyl. Acetyl is most preferred.

In the formula (11), $R^1$ is linear or branched chain alkyl having from 2 to 20 carbon atoms, preferably 6 to 8 carbon atoms, such as n-hexyl, n-heptyl and n-octyl with n-heptyl being most preferred. X is halogen, such as chlorine, bromine and iodine with chlorine being most preferred.

In the formula (9), A and $R^5$ are the same as defined in the formula (10), and $R^1$ is the same as defined in the formula (11).

A method for reacting the compound of the formula (10) and the compound of the formula (11) is not particularly limited, and it can be carried out by well-known methods. The methods include, for example, Friedel-Crafts reaction wherein the compound of the formula (10) is reacted with the compound of the formula (11) in the presence of Lewis acid, such as anhydrous aluminum trichloride, anhydrous aluminum tribromide, anhydrous zinc chloride, anhydrous ferric chloride, anhydrous titanium tetrachloride, boron trifluoride or anhydrous tin chloride. Any solvents which are inactive in the reaction may be used. Examples of such solvents include 1,2-dichloroethane, dichloromethane, chloroform, tetrachloromethane, nitrobenzene and carbon disulfide. A reaction temperature ranges from −78 to 90° C. A reaction time varies depending on the reaction conditions, but it usually ranges from 30 minutes to 2 days.

In the method, the compound of the formula (10) is preferably dissolved in the solvent in the content ranging from 1 to 70% by weight, the catalyst is preferably used in the amount of 1 to 5 moles per 1 mole of the compound of the formula (10). The compound of the formula (9) obtained by the above-mentioned step can be purified by well-known method in the field of organic chemistry, such as recrystallization, chromatography, distillation, extraction by the solvent and ion exchange process.

Next, the detailed description will be made on the step B. In the step B, the compound of formula (5) is prepared by deacylating the compound of the formula (9).

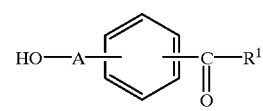

(5)

In the formula (5), A is the same as defined in the formula (10), and $R^1$ is the same as defined in the formula (11).

A method for deacylating the compound of the formula (9) is not particularly limited, and it can be carried out by well-known methods which include, for example, the method for ester exchange or hydrolysis of the compound of the formula (9) with a base such as sodium methylate, sodium ethylate, sodium hydroxide, potassium hydroxide and lithium hydroxide, or an acid such as hydrochloric acid and sulfuric acid. Any of known solvents which are inactive in the reaction may be used, for example, methanol, ethanol, isopropyl alcohol, tetrahydrofuran, dioxane, water, and mixture thereof. A reaction temperature ranges from −25° C. to boiling point of the solvent. A reaction time varies depending on the reaction conditions, but it usually ranges from 30 minutes to 2 days.

In the method, the compound of the formula (9) is preferably dissolved in the solvent in the content ranging from 1 to 70% by weight, and the base or the acid is preferably used in the amount of 0.01 to 2 moles per 1 mole of the compound of the formula (9). The compound of the formula (5) obtained by the above-mentioned step can be purified by well-known method in the field of organic chemistry, such as recrystallization, chromatography, distillation, extraction by the solvent and ion exchange process.

Next, the detailed description will be made on the step D. In the step D, the compound of formula (7) is prepared by converting hydroxyl group of the compound of the formula (5) to a leaving group.

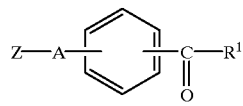

(7)

In the formula (7), A is the same as defined in the formula (10), $R^1$ is the same as defined in the formula (11), and Z is a leaving group. Z includes, for example, halogen such as chlorine, bromine, iodine, p-toluene sulfonyloxy, methane sulfonyloxy, and trifluoromethane sulfonyloxy.

A method for converting the hydroxyl group of the compound of the formula (5) to a leaving group is not particularly limited, and it can be carried out by well-known methods which include, for example, the method for halogenation of the compound of the formula (5) by using thionyl chloride, thionyl bromide, hydrogen chloride, hydrogen bromide, phosphorus trichloride, phosphorus tribromide, phosphorus pentachloride, phosphorus pentabromide, chlorine, bromine, iodine, tetrachloromethane, tetrabromomethane, N-chloro succinic imide, N-bromo succinic imide, sodium chloride, sodium bromide or sodium iodide, and the method for converting the compound of the formula (5) to a sulfonate by using p-toluenesulfonyl chloride, methanesulfonyl chloride, trifluoromethanesulfonyl chloride, anhydrous p-toluenesulfonic acid, anhydrous methanesulfonic acid or anhydrous trifluoromethanesulfonic acid. In the step D, two-step reaction: conversion of the compound of the formula (5) to a sulfonate; and halogenation of the sulfonate by using sodium chloride, sodium bromide or sodium iodide may be carried out. Any solvents which are inactive in the reaction may be used, for example, ethyl acetate, benzene, toluene, dichloroethane, 1,2-dichloroethane, pyridine, N,N-dimethylformamide, diethyl ether, tetrachloromethane, chloroform, acetonitrile, 2-butanone, acetone and the mixture thereof. In the reaction, the auxiliary such as pyridine, triethylamine, imidazole, dimethylaminopyridine, triphenylphosphine, triphenyl phosphonate, sulfuric acid and the mixture thereof preferably may be used. A reaction temperature ranges from −25° C. to boiling point of the solvent. A reaction time varies depending on the reaction conditions, but it usually ranges from 30 minutes to 2 days.

In the method, the compound of the formula (5) is preferably dissolved in the solvent in the content ranging from 1 to 70% by weight, reagent for halogenation or reagent for sulfonylation is preferably used in the amount of 1 to 50 moles per 1 mole of the compound of the formula (5). The compound of the formula (7) obtained by the above-mentioned step can be purified by well-known method in the field of organic chemistry, such as recrystallization, chromatography, distillation, extraction by the solvent and ion exchange process.

Next, the detailed description will be made on the step J. In the step J, the compound of the formula (6) is prepared by reacting the compound of the formula (7) and 2-(N-substituted)aminomalonic diester of the formula (3).

(3)

In the formula (3), $R^2$ and $R^3$ are the same or different, and are lower alkyl or aralkyl. The lower alkyl includes, for example, methyl, ethyl, n-propyl, isopropyl, n-butyl, isobutyl and tertiary butyl. The aralkyl includes, for example, benzyl, nitrobenzyl, methoxybenzyl and methylbenzyl. Ethyl is preferred. $R^4$ is a protecting group which is used in the field of synthetic organic chemistry, and includes, for example, acetyl, benzoyl, tertiary butoxycarbonyl and benzyloxycarbonyl. Acetyl is preferred.

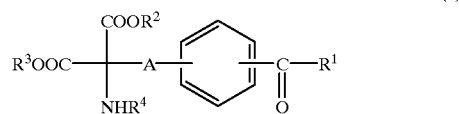

(6)

In the formula (6), A is the same as defined in the formula (10), $R^1$ is the same as defined in the formula (11), and $R^2$, $R^3$ and $R^4$ are the same as defined in the formula (3).

A method for preparing the compound of the formula (6) by reacting the compound of the formula (7) and the 2-(N-substituted)aminomalonic diester is not particularly limited, and it can be carried out by well-known methods which include, for example, the method for condensation of the compound of the formula (7) and the 2-(N-substituted) aminomalonic diester of the formula (3) in the presence of a base such as sodium ethylate, sodium hydride, sodium methylate and sodium. Any known solvents which are inactive in the reaction may be used, for example, ethanol, methanol, tetrahydrofuran, N,N-dimethylformamide, toluene, dimethyl sulfoxide and the mixture thereof. A reaction temperature ranges from −20° C. to boiling point of the solvent. A reaction time varies depending on the reaction conditions, but it usually ranges from 30 minutes to 2 days.

In the method, the compound of the formula (7) is preferably dissolved in the solvent in the content ranging from 1 to 70% by weight, 2-(N-substituted)aminomalonic diester of the formula (3) and the base are preferably used in the amount of 1 to 10 moles per 1 mole of the compound of the formula (7). The compound of the formula (6) obtained by the above-mentioned step can be purified by well-known method in the field of organic chemistry, such as recrystallization, chromatography, distillation, extraction by the solvent and ion exchange process.

By the way, in the step J, the compound of the formula (21) is produced as by-product. The compound of the formula (6) can be obtained by reacting the compound of the formula (21) and the 2-(N-substituted)aminomalonic diester of the formula (3) under the same reaction conditions of the above-mentioned step.

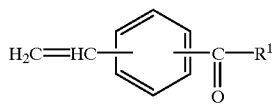

(21)

In the formula (21), $R^1$ is the same as defined in the formula (11).

Next, the detailed description will be made on the step K. In the step K, the compound of the formula (1) is prepared by reducing ketone group of the compound of the formula (6) to methylene group.

A method for reducing the ketone group of the compound of formula (6) to methylene group is not particularly limited, and it can be carried out by well-known method which include, for example, the method for hydrogenating the compound of formula (6) by hydrogen or sodium borohydride in the presence of palladium catalyst (palladium carbon, palladium, palladium barium sulfate, palladium chloride and the like) or nickel catalyst (Raney Nickel, nickel acetate and the like). Any known solvents which are inactive in the reaction may be used. Ethanol, methanol, ethyl acetate, dioxane, water and the mixture thereof are preferred. It is possible to promote a reaction by adding an acid such as hydrochloric acid and acetic acid, or by applying a pressure. A reaction temperature ranges from −25° C. to boiling point of the solvent. A reaction time varies depending on the reaction conditions, but it usually ranges from 30 minutes to 20 days.

In the method, the compound of formula (6) is preferably dissolved in the solvent in the content ranging from 1 to 70% by weight, and the catalyst is preferably used in the amount of 0.001 to 20 g per 1 g of the compound of formula (6). The compound of the formula (1) obtained by the above-mentioned step can be purified by well-known method in the field of organic chemistry, such as recrystallization, chromatography, distillation, extraction by the solvent and ion exchange process.

Next, the detailed description will be made on the step N. In the step N, the compound of the formula (7) is prepared by reacting the compound of the formula (15) and the compound of the formula (11).

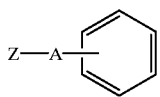

(15)

In the formula (15), A is the same as defined in the formula (10), and Z is the same as defined in the formula (7).

A method for preparing the compound of the formula (7) by reacting the compound of the formula (15) and the compound of the formula (11) is not particularly limited, and it can be carried out by well-known method which include, for example, a method similar to the step A.

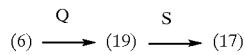

Next, the detailed description will be made on the process for preparing 2-amino-1,3-propanediol derivatives of the present invention. A process for preparing 2-amino-1,3-propanediol derivatives of the present invention uses the compound of the formula (6) as starting material, and comprises the following synthetic route, as shown in FIG. 1.

First, the detailed description will be made on the step Q. In the step Q, the compound of the formula (19) is prepared by the steps of reducing ester and ketone groups of the compound of the formula (6) to hydroxymethyl and hydroxymethylene groups, protecting the hydroxyl groups with a protecting group which is well-known in the field of organic chemistry, if necessary, and removing the protecting group, if necessary.

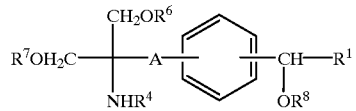

(19)

In the formula (19), A is the same as defined in the formula (10), $R^1$ is the same as defined in the formula (11), $R^4$ is hydrogen or a protecting group for an amino group, which is widely used in synthetic organic chemistry, and include, for example, acetyl group, benzoyl group, tertiary-butoxycarbonyl group and benzyloxycarbonyl group. Hydrogen or acetyl group is preferred. $R^6$, $R^7$ and $R^8$ are the same or different, and are hydrogen or protecting group for hydroxyl group, which is widely used in synthetic organic chemistry, and include, for example, acetyl group, benzoyl group, benzyl group, trimethylsilyl group, tertiary-butyldimethylsilyl group, methoxymethyl group and tetrahydropyranyl group. Acetyl group or hydrogen is preferred.

A method for reducing ester and ketone groups of the compound of the formula (6) to hydroxymethyl and hydroxymethylene groups is not particularly limited, and it can be carried out by well-known method which includes, for example, the method for reducing the compound of the formula (6) with a metal hydride reducing agent such as sodium borohydride, lithium borohydride and lithium aluminum hydride, or diborane. Any known solvents which are inactive in the reaction may be used, for example, methanol, ethanol, tertiary-butyl alcohol, tetrahydrofuran, diethyl ether, ethylene glycol dimethyl ether, and the mixture thereof. A reaction temperature ranges from −25° C. to boiling point of the solvent. A reaction time varies depending on the reaction conditions, but is usually ranges from 30 minutes to 2 days.

In the method, the compound of the formula (6) is preferably dissolved in the solvent in the content ranging from 1 to 70% by weight, and the reducing agent is preferably used in the amount ranging from 1 to 20 moles per 1 mole of the compound of the formula (6). After the compound of the formula (6) is reduced, or the reduced compound is protected by the protecting group, if necessary, or the protecting group is removed, if necessary, the compound can be purified by well-known method in the field of organic chemistry, such as recrystallization, chromatography, distillation, extraction by the solvent and ion exchange process.

Next, the detailed description will be made on the step S. In the step S, the compound of the formula (17) is prepared by reducing hydroxymethylene or substituted oxymethylene group of the compound of the formula (19) to methylene group.

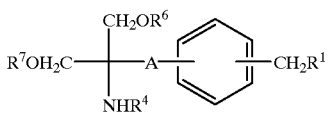

(17)

In the formula (17), A is the same as defined in the formula (10), $R^1$ is the same as defined in the formula (11), and $R^4$, $R^6$ and $R^7$ are the same as defined in the formula (19).

A method for reducing hydroxymethylene or substituted oxymethylene group of the compound of the formula (19) to methylene group is not particularly limited, and it can be carried out by well-known method which includes, for example, a method similar to the step K.

Next, the detailed description will be made on the compound of the formula (5), the compound of the formula (7) and the compound of the formula (6) of the present invention.

The compound of the formula (5) is an intermediate which is used for preparing 2-amino malonic acid derivatives of the present invention, and has the following formula:

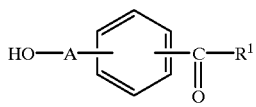

(5)

wherein A and $R^1$ are the same as defined in the formula (1).

A method for preparing the compound of the formula (5) of the present invention is not particularly limited. For example, it can be prepared by deacylating the compound of the formula (9) as described in the process for preparing 2-amino malonic acid derivatives of the present invention. The compound of the formula (5) is obtained in the form of crystal. Accordingly, it can be purified readily, and it is useful as an intermediate for preparing 2-amino malonic acid derivatives which are intermediates for preparing 2-amino-1,3-propanediol derivatives.

Next, the detailed description will be made on the compound of the formula (7). The compound of the formula (7) is an intermediate which is used for preparing the 2-amino malonic acid derivatives of the present invention, and has the following formula:

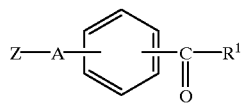

(7)

wherein A and $R^1$ are the same as defined in the formula (1), and Z is a leaving group.

A method for preparing the compound of the formula (7) of the present invention is not particularly limited. For example, it can be prepared by converting hydroxyl group of the compound of the formula (5) to a leaving group, as explained above for the production of 2-amino malonic acid derivatives. The compound of the formula (7) is obtained in the form of crystal. Accordingly, it can be purified readily, and it is useful for an intermediate for preparing 2-amino malonic acid derivatives which are intermediates for preparing 2-amino-1,3-propanediol derivatives.

Next, the detailed description will be made on the compound of the formula (6). The compound of the formula (6) is an intermediate which is used for preparing 2-amino malonic acid derivatives of the present invention, and has the following formula:

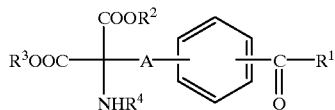

(6)

wherein A, $R^1$, $R^2$, $R^3$ and $R^4$ are the same as defined in the formula (1).

A method for preparing the compound of the formula (6) of the present invention is not particularly limited. For example, it can be prepared by reacting the compound of the formula (7) and 2-(N-substituted)amino malonic diester of the formula (3). The compound of the formula (6) is obtained in the form of crystal. Accordingly, it can be purified readily, and it is useful for an intermediate for preparing 2-amino malonic acid derivatives which are intermediates for preparing 2-amino-1,3-propanediol derivatives.

The following Examples will further illustrate the present invention, which by no means limit the present invention.

EXAMPLE 1

Step A: Preparation of 2-(4-octanoyl phenyl)ethyl acetate (9)

Octanoyl chloride (216 g) and phenetyl acetate (285 g) were dissolved in 1,2-dichloroethane to obtain a solution. Then aluminum chloride (372 g) was added to the solution with cooling little by little. After adding aluminum chloride, the solution was stirred at room temperature for 2 hours. The solution was stirred for further 30 minutes, and then was poured into ice water. Dichloroethane layer was taken, washed with water, dried over anhydrous magnesium sulfate, and concentrated. The residue was distilled under vacuum to obtain a fraction which contains 2-(4-octanoyl phenyl)ethyl acetate as a major component (280 g).

TLC Rf: 0.3(hexane/ethyl acetate=5/1, silica gel 60F$_{254}$ plate); EIMS m/z: 230 (M—CH$_3$COOH)$^+$, 191, 159, 146, 131.

Step B: Preparation of 4'-(2-hydroxy ethyl)octanophenone (5)

A solution (18.8 ml) of 28% sodium methylate in methanol was added to a solution of the material (280 g) which contains 2-(4-octanoyl phenyl)ethyl acetate obtained in the step A as a major component in methanol (200 ml), and the solution was stirred at room temperature for 1 hour. Suspension of Amberlite IR-120B in methanol (98 ml) was added to the solution, and the mixture was filtered. The filtrate was concentrated, and the residue was recrystallized from hexane-ethyl acetate (10:1) to obtain 4'-(2-hydroxy ethyl)octanophenone (138 g) in the form of colorless crystal.

TLC Rf: 0.4(hexane/ethyl acetate=2/1, silica gel 60F$_{254}$plate); melting point: 47.4° C.; IR (KBr) 3260, 2910, 2850, 1680 cm$^{-1}$; UV $\lambda_{max}$ (MeOH) nm ($\epsilon$): 216.4 (3047), 261.2 (4421); $^1$H-NMR (500 MHz, CDCl$_3$) $\delta$: 7.91 (2H, d, J=8.3 Hz, C$_6$—H$_2$), 7.32 (2H,d, J=8.5 Hz, C$_6$—H$_2$), 3.90 (2H, t, J=6.6 Hz, CH$_2$OH), 2.94 (2H, t, J=7.3 Hz, COCH$_2$), 2.93 (2H, t, J=6.6 Hz, Ph—CH$_2$), 1.72 (2H, qui, J=7.3 Hz, CH$_2$), 1.59 (1H, br s, OH), 1.40~1.26 (8H, m, CH$_2$×4), 0.88 (3H, t, J=7.1 Hz, CH$_3$). EIMS m/z: 248 (M)$^+$, 230, 203, 177, 164, 149.

Step D-1: Preparation of 2-(4-octanoyl phenyl)ethyl p-toluene sulfonate (7)

4'-(2-Hydroxy ethyl)octanophenone (1.0 g) prepared in the step B was dissolved in dichloromethane (10 ml) to obtain a solution. p-Toluene sulfonyl chloride (923 mg) and pyridine (383 mg) were added to the solution with cooling, and the mixture was stirred at room temperature for 2 hours. After the reaction, ice water was added to the solution, the solution was stirred at room temperature for 20 minutes. Dichloromethane layer was washed with 2% hydrochloric acid, sodium bicarbonate solution, and water. The dichloromethane layer was dried over anhydrous sodium sulfate, and concentrated. The residue was recrystallized from hexane-ethyl acetate (10:1) to obtain 2-(4-octanoyl phenyl) ethyl p-toluene sulfonate (950 mg) in the form of colorless crystal.

TLC Rf: 0.4(hexane/ethyl acetate=3/1, silica gel 60$F_{254}$ plate); melting point: 59~60° C.; IR (KBr) 2960, 2850, 1680, 1360, 1170, 960, 920, 810, 660, 550 cm$^{-1}$; $^1$H-NMR (500 MHz, CDCl$_3$) δ: 7.83 (2H, d, J=8.3 Hz, $C_6$—$H_2$), 7.67 (2H, d, J=8.3 Hz, $C_6$—$H_2$), 7.26 (2H, d, J=8.5 Hz, $C_6$—$H_2$), 7.19 (2H, d, J=8.5 Hz, $C_6$—$H_2$), 4.24 (2H, t, J=6.8 Hz, TsOCH$_2$), 3.00 (2H, t, J=6.8 Hz, Ph—CH$_2$), 2.92 (2H,t, J=7.3 Hz, COCH$_2$), 2.42 (3H, s, Ph—CH$_3$), 1.72 (2H,qui, J=7.3 Hz, CH$_2$), 1.40~1.26 (8H, m, CH$_2$X4), 0.88 (3H, t, J=7.1 Hz, CH$_3$); EIMS m/z: 303 (M—(CH$_2$)$_6$CH$_3$)$^+$, 230, 146, 131, 91.

Step D-2: Preparation of 4'-(2-iodoethyl)octanophenone (7)

2-(4-Octanoyl phenyl)ethyl p-toluene sulfonate (1.23 g) prepared in the above-described procedure was dissolved in 2-butanone (18 ml) to obtain a solution. Sodium iodide (550 mg) was added to the solution, and the solution was heated to reflux for 40 minutes. The reaction solution was concentrated, and the solution was partitioned with water-dichloromethane. The dichloromethane layer was washed with water, dried over anhydrous sodium sulfate, and concentrated to obtain 4'-(2-iodoethyl)octanophenone (1.09 g) in the form of white crystal.

TLC Rf: 0.3(Hexane/EtOAc=20/1, silica gel 60$F_{254}$ plate); melting point: 36.5° C.; IR (KBr) 2950, 2920, 2850, 1680, 1600, 1230 cm$^{-1}$; UV $λ_{max}$ (MeOH) nm (ε): 215.8 (4371), 256.2 (6356). $^1$H-NMR (500 MHz, CDCl$_3$) δ: 7.90 (2H, d, J=8.3 Hz, $C_6$—$H_2$), 7.26 (2H, d, J=8.1 Hz, $C_6$—$H_2$), 3.35 (2H, t, J=7.3 Hz, CH$_2$), 3.22 (2H, t, J=7.6 Hz, CH$_2$), 2.92 (2H, t, J=7.6 Hz, COCH$_2$), 1.71 (2H, qui, J=7.1 Hz, CH$_2$), 1.36~1.25 (8H, m, CH$_2$×4), 0.86 (3H, t, J=6.8 Hz, CH$_3$); EIMS m/z: 274 (M—CH=CH(CH$_2$)$_3$CH$_3$)$^+$, 259, 203, 147.

Step D-3: Preparation of 4'-(2-iodoethyl)octanophenone (7)

4'-(2-Hydroxy ethyl)octanophenone prepared in the step B (137 g), imidazole (53 g) and triphenyl phosphine (174 g) were dissolved in ethyl acetate (550 ml) to obtain a solution. Iodine (197 g) was added to the solution with cooling, and the solution was stirred at room temperature for 1 hour. Then the reaction solution was diluted with ethyl acetate, the solution was washed with saturated sodium sulfite solution, and saturated saline solution, dried over anhydrous magnesium sulfate, and concentrated. The concentrated residue was extracted with hexane-ethyl acetate (20:1), and extracted solution was passed through a silica gel layer. The filtrate was concentrated to obtain 4'-(2-iodoethyl) octanophenone (175 g) in the form of white crystal.

Step J-1: Preparation of diethyl acetamide-2-(4-octanoyl phenyl)ethyl malonate (6)

4'-(2-Iodoethyl)octanophenone (175 g) prepared in the step D-3 was dissolved in anhydrous tetrahydrofuran (700 ml) to obtain 4'-(2-iodoethyl)octanophenone solution. Diethyl acetamide malonate (320 g) and sodium ethylate (100 g) was dissolved in anhydrous ethanol (1050 ml), and the 4'-(2-iodoethyl)octanophenone (175 g) solution was added, and the solution was heated to reflux for 7 hours. Tetrahydrofuran was removed by distillation from the solution. The solution was poured into ice water to obtain a precipitate which was recrystallized from hexane-ethyl acetate (40:1) to obtain diethyl acetamide-2-(4-octanoyl phenyl)ethyl malonate (110 g) in the form of colorless crystal.

TLC Rf: 0.5(hexane/ethyl acetate=1/1, silica gel 60$F_{254}$ plate); melting point: 79.0° C.; IR (KBr) 3250, 2930, 2850, 1750, 1680, 1650, 1520, 1260, 1220, 1200 cm$^{-1}$; UV $λ_{max}$ (MeOH) nm (ε): 216.7 (5487), 256.7 (7810); $^1$H-NMR (500 MHz, CDCl$_3$) δ: 7.84 (2H, d, J=8.3 Hz, $C_6$—$H_2$), 7.21 (2H, d, J=8.1 Hz, $C_6$—$H_2$), 6.75 (1H, br s, NH), 4.20 (2H, q,J=6.8 Hz, OCH$_2$CH$_3$), 4.19 (2H,q,J=7.1 Hz, OCH$_2$CH$_3$), 2.90 (2H, t, J=7.3 Hz, COCH$_2$), 2.69 (2H, m, Ph—CH$_2$), 2.51 (2H, m, CH$_2$), 1.96 (3H, s, Ac), 1.69 (2H, qui, J=7.3 Hz, CH$_2$), 1.32 (2H, m, CH$_2$), 1.27 (6H, m, CH$_2$×3), 1.23 (6H,t,J=7.1 Hz, OCH$_2$CH$_3$×2), 0.86 (3H, J=6.8 Hz, CH$_3$); EIMS m/z: 402 (M—OCH$_2$CH$_3$)$^+$, 332, 231, 217, 171, 131.

Step J-2: Preparation of diethyl acetamide-2-(4-octanoyl phenyl)ethyl malonate (6)

4'-(2-Iodoethyl)octanophenone prepared (5 g) in the step D-3 was dissolved in anhydrous N,N-dimethylformamide (15 ml) to obtain 4'-(2-iodoethyl)octanophenone solution. Diethyl acetamide malonate (9.09 g) was dissolved in anhydrous N,N-dimethylformamide (30 ml) to obtain a solution to which 60% sodium hydride oil dispersion (1.23 g) was added with cooling. The solution was stirred under atmosphere of nitrogen for 1 hour. 4'-(2-Iodoethyl) octanophenone solution was added to the solution, and the solution was stirred under atmosphere of nitrogen at 60° C. for 2 hours. The reaction solution was poured into ice water, and extracted with ether, and washed with saturated saline solution. The extracted solution was dried over anhydrous magnesium sulfate, and concentrated. The residue was subjected to silica gel column chromatography using hexane-ethyl acetate (1:0→3:1) as an eluate to obtain diethyl acetamide-2-(4-octanoyl phenyl)ethyl malonate (3.2 g) and 4'-vinyl octanophenone (1.5 g) in the form of colorless crystal, respectively. The diethyl acetamide malonate (4.25 g) was dissolved in anhydrous N,N-dimethylformamide (30 ml) to obtain a solution, to which 60% sodium hydride oil dispersion (574 mg) was added. The solution was stirred under atmosphere of nitrogen at room temperature for 30 minutes. 4'-Vinyl octanophenone (1.5 g) and anhydrous ethanol (7.5 ml) were added to the solution, and the solution was stirred under atmosphere of nitrogen at 60° C. for 6 hours, and the solution was stirred at room temperature for 2 days. The reaction solution was poured into ice water, extracted with ether, and washed with saturated saline solution. The extracted solution was dried over anhydrous magnesium sulfate, and concentrated. The residue was subjected to silica gel column chromatography using hexane-ethyl acetate (1:0→4:1) as an eluate to obtain diethyl acetamide-2-(4-octanoyl phenyl)ethyl malonate (2.29 g) in the form of colorless crystal.

4'-vinyl octanophenone: TLC Rf: 0.4(hexane/ethyl acetate=20:1, silica gel 60$F_{254}$ plate); IR (KBr) 2920, 2850, 1670, 1470, 1410, 1320, 1280, 990, 910, 860 cm$^{-1}$; $^1$H-NMR (400 MHz, CDCl$_3$) δ: 7.92 (2H, d, J=8.3 Hz, $C_6$—$H_2$), 7.47 (2H, d, J=8.3 Hz, $C_6$—$H_2$), 6.75(1H, dd, J=17.6 and 10.9 Hz, CH=), 5.86(1H, d, J=17.7 Hz, CHa=), 5.38 (1H, d, J=10.9 Hz, CHb=), 2.94 (2H, t, J=7.3 Hz, COCH$_2$), 1.73 (2H, qui, J=7.3 Hz, CH$_2$), 1.35~1.29 (8H, m, CH$_2$×4), 0.88 (3H, t, J=6.8 Hz, CH$_3$); $^{13}$C-NMR(400 MHz, CDCl$_3$) δ: 200.1, 141.9, 136.3, 136.0, 128.7, 128.5 126.3, 116.5, 38.7, 31.7, 29.4, 29.2, 24.5, 22.6, 14.1; EIMS m/z: 230 (M)$^+$, 159, 146, 131, 103, 77.

Step J-3: Preparation of diethyl acetamide-2-(4-octanoyl phenyl)ethyl malonate (6)

2-(4-Octanoyl phenyl)ethyl p-toluene sulfonate prepared in the step D-1 (500 mg), diethyl acetamide malonate (810 mg) and sodium ethylate (313 mg) were dissolved in anhydrous ethanol (1.5 ml)—anhydrous N,N-dimethylformamide (6 ml) to obtain a solution. The solution was stirred under atmosphere of nitrogen at 60° C. overnight. The reaction solution was poured into ice water, extracted with ether, and washed with saturated saline solution. The extracted solution was dried over anhydrous magnesium sulfate, and concentrated. The residue was subjected to silica gel column chromatography using hexane-ethyl acetate (1:0→3:1) as an eluate to obtain diethyl acetamide-2-(4-octanoyl phenyl)ethyl malonate (417 mg) in the form of colorless crystal.

Step K: Preparation of diethyl acetamide-2-(4-octyl phenyl) ethyl malonate (1)

Diethyl acetamide-2-(4-octanoyl phenyl)ethyl malonate prepared in the step J (923 g) was stirred in ethanol (10 L) under atmosphere of hydrogen in the presence of 5% palladium carbon (138 g) overnight. The catalyst was removed by filtration, and the filtrate was concentrated. The residue was recrystallized from hexane to obtain diethyl acetamide-2(4-octyl phenyl)ethyl malonate (670 g) in the form of colorless crystal.

TLC Rf: 0.6(hexane/ethyl acetate=1/1, silica gel 60F$_{254}$ plate); melting point: 61.0° C.; IR (KBr) 3300, 2920, 2850, 1750, 1650, 1520, 1220, 1200 cm$^{-1}$; UV λ$_{max}$ (MeOH) nm (ε): 219.1 (5017), 259.2 (303.5), 264.5 (392.4), 272.7 (357.7); $^1$H-NMR (270 MHz, DMSO-d$_6$) δ: 8.32 (1H, brs, NH), 7.08 (2H, d, J=7.9 Hz, C$_6$—H$_2$), 7.02 (2H, d, J=7.9 Hz, C$_6$—H$_2$), 4.13 (4H, q, J=7.3 Hz, OCH$_2$CH$_3$X2), 2.52 (4H, m, Ph—CH$_2$X$_2$), 2.37 (2H, m, CH$_2$), 1.94 (3H, s, Ac), 1.52 (2H, m, CH$_2$), 1.24 (10H, m, CH$_2$X5), 1.15 (6H, t, J=7.3 Hz, OCH$_2$CH$_3$X2), 0.85 (3H, t, J=6.6 Hz, CH$_3$); EIMS m/z: 388 (M—OCH$_2$CH$_3$)$^+$, 318, 301, 244, 217, 171, 143.

Step Q-1: Preparation of 1-(4-(3-acetamide-4-acetoxy-3-acetoxymethyl)butyl phenyl)octyl acetate (19)

Diethyl acetamide-2-(4-octanoyl phenyl)ethyl malonate prepared in the step J (5.0 g) was dissolved in methanol (20 ml) to obtain a solution. Sodium borohydride (2.7 g) was added to the solution, and stirred at room temperature for 3.5 hours. The reaction solution was diluted with ethyl acetate, and washed with 1N-HCl, saturated sodium bicarbonate solution and saturated saline solution. Obtained ethyl acetate layer was dried over anhydrous magnesium sulfate, and concentrated. Pyridine (10 ml) and acetic anhydride (20 ml) were added to the residue, and it was stirred at 50° C. for 2 hours. The reaction solution was poured into ice water to obtain a precipitate. The precipitate was recrystallized from hexane-ethyl acetate (4:1) to obtain 1-(4-(3-acetamide-4-acetoxy-3-acetoxymethyl)butyl phenyl)octyl acetate (4.09 g) in the form of colorless crystal.

TLC Rf: 0.3(hexane/ethyl acetate=1/2, silica gel 60F$_{254}$ plate); IR (KBr) 3310, 2930, 2860, 1740, 1650, 1560, 1470, 1380, 1230, 1060 cm$^{-1}$; $^1$H-NMR (500 MHz, CDCl$_3$) δ: 7.23 (2H, d, J=8.1 Hz, C$_6$—H$_2$), 7.15 (2H, d, J=8.1 Hz, C$_6$—H$_2$), 5.67 (1H, t, J=7.0 Hz, CH), 5.66 (1H, brs, NH), 4.34 (4H, s, OCH$_2$X2), 2.59 (2H, m, Ph—CH$_2$), 2.20 (2H, m, Ph—CH$_2$), 2.08 (6H, s, OAcX2), 2.04 (3H, s, OAc), 1.94 (3H, s, NAc), 1.80~1.84 (1H, m, CHCHa), 1.76~1.68 (1H, m, CHCHb), 1.29~1.21 (10H, m, CH$_2$X5), 0.86 (3H, t, J=7.1 Hz, CH$_3$); FAB-MS m/z: 492 (M+H)$^+$, 432, 372.

Step S-1: Preparation of 2-acetamide-2-acetoxy methyl-4-(4-octyl phenyl)butyl acetate (17)

1-(4-(3-Acetamide-4-acetoxy-3-acetoxymethyl)butyl phenyl)octyl acetate prepared in the step Q-1 (100 mg) was stirred in ethyl acetate (2 ml) under atmosphere of hydrogen in the presence of 5% palladium carbon overnight. The catalyst was removed by filtration, and the filtrate was concentrated to obtain 2-acetamide-2-acetoxy methyl-4-( 4-octyl phenyl)butyl acetate in the form of colorless crystal (92 mg).

TLC Rf: 0.4(hexane/ethyl acetate=2/1, silica gel 60F$_{254}$ plate); melting point: 111.8° C.; IR (KBr) 3320, 2910, 2850, 1740, 1650, 1550, 1470, 1390, 1260, 1240, 1050 cm$^{-1}$; UV λ$_{max}$ (MeOH) nm (ε): 217.6 (4772), 259.0 (305.7), 264.5 (394.6), 272,8 (368.6); $^1$H-NMR (270 MHz, DMSO-d$_6$) δ: 7.63 (1H, brs, NH), 7.07 (4H, s, C$_6$—H$_4$), 4.28 (2H, d, J=10.6 Hz, CHaOX2), 4.18 (2H, d, J=10.6 Hz, CHbOX2), 2.5 (4H, m, Ph—CH$_2$X2), 2.02 (6H, s, OAcX2), 1.94 (2H, m, CH$_2$), 1.85 (3H, s, NAc), 1.52 (2H,m, CH$_2$), 1.24 (10H, m, CH$_2$X5), 0.85 (3H, t, J=7.2 Hz, CH$_3$); EIMS m/z: 433 (M)$^+$, 373, 260, 216, 157, 117, 105, 97.

Step Q-2 Preparation of 2-amino-2-(4-(2-hydroxy octyl) phenyl)ethyl propane-1,3-diol (19)

1-(4-(3-Acetamide-4-acetoxy-3-acetoxymethyl)butyl phenyl)octyl acetate prepared in the step Q-1 was heated to reflux in methanol (7 ml)—1N sodium hydroxide (10.2 ml) for 4 hours. The reaction solution was diluted with water, and extracted with chloroform three times. The extracted solutions were combined and concentrated to obtain 2-mino-2-(4-(1-hydroxy octyl)phenyl)ethyl propane-1,3-diol (690 mg) in the form of wax-like solid.

TLC Rf: 0.5(chloroform/methanol/acetic acid/water=70/20/6/4, silica gel 60F$_{254}$ plate); IR (KBr) 3340, 2930, 2860, 1460, 1430, 1240, 1060, 1010, 950, 857 cm$^{-1}$; $^1$H-NMR (270 MHz, DMSO-d$_6$) δ: 7.18 (2H, d, J=8.1 Hz, d, J=8.1 Hz, C$_6$—H$_2$), 7.10 (2H, d, J=8.1 Hz, d, J=8.1 Hz, C$_6$—H$_2$) 5.00 (1H, s, OH), 4.47 and 4.43 (1H, brs, OH respectively), 4.45 (1H, m, CH), 3.25 (2H, d, J=10.5 Hz, OCHaX2), 3.21 (2H, d, J=10.3 Hz, CHbX2), 2.55 (2H, m, Ph—CH$_2$), 1.60~1.53 (1H, m, CHCHa), 1.53~1.49 (1H, m, CHCHb), 1.47 (2H, m, CH$_2$), 1.30 (2H, brs, NH$_2$), 1.27 (10H, m, CH$_2$X5), 0.84 (3H, t, J=7.1 Hz, CH$_3$); FAB-MS m/z: 324 (M+H)$^+$.

Step S-2: Preparation of 2-amino-2-(4-octyl phenyl)ethyl propane-1,3-diol hydrochloride (17)

2-Amino-2-(4-(1-hydroxy octyl)phenyl)ethyl propane-1, 3-diol prepared in the step Q-2 (100 mg) was stirred in ethanol (1.7 ml)—1N hydrochloric acid ethanol (0.32 ml) under atmosphere of hydrogen in the presence of 5% palladium carbon overnight. The catalyst was removed by filtration, and the filtrate was concentrated to obtain 2-amino-2-(4-octyl phenyl)ethyl propane-1,3-diol hydrochloride (106 mg) in the form of colorless crystal.

TLC Rf: 0.55(chloroform/methanol/acetic acid/water=70/20/6/4, silica gel 60F$_{254}$ plate); decomposition temperature: 260° C.; IR (KBr) 3400(sh), 3250, 3050(sh), 2910, 2850, 1580, 1520, 1470, 1060 cm$^{-1}$; UV λ$_{max}$ (H$_2$O) nm (ε): 210.7 (4709), 264 (392.4), 272 (341.1); $^1$H-NMR (500 MHz, DMSO-d$_6$) δ: 7.91 (3H, brs, NH$_3$$^+$), 7.09 (2H, d, J=8.5 Hz, C$_6$—H$_2$), 7.07 (2H, d, J=8.5 Hz, C$_6$—H$_2$), 5.38 (2H, brs, OHX2), 3.51 (4H, s, CH$_2$OX2), 2.56 (2H, m, Ph—CH$_2$), 2.49 (2H, Ph—CH$_2$), 1.77 (2H, m, CH$_2$), 1.51 (2H, m, CH$_2$), 1.25 (10H, m, CH$_2$X5), 0.83 (3H, t, J=7.5 Hz, CH$_3$); EIMS m/z: 276 (M—CH$_2$OH)$^+$, 117, 105.

Step N: Preparation of 4-(2-bromo ethyl)octanophenone (7)

(2-Bromoethyl)benzene (5.0 g) and octanoyl chloride (4.83 g) were dissolved in dichloromethane (40 ml) to obtain a solution. Aluminum chloride (3.67 g) was added to the solution at −20° C., and the solution was stirred at −20° C. for 1 hour, and at room temperature overnight. The reaction solution was added to ice water, and extracted with ether. The extracted solution was washed with 1N hydrochloric acid, saturated saline solution, saturated sodium icarbonate and saturated saline solution. Obtained ether layer was dried over anhydrous magnesium sulfate, and concentrated. The concentrated residue was subjected to silica gel column chromatography using hexane-ethyl acetate (80:1→20:1) as an eluate to obtain a fraction which contains 4'-(2-bromoethyl)octanophenone as a major component (6.96 g) in the form of oily substance.

TLC Rf: 0.3(hexane/ethyl acetate=20:1, silica gel 60F$_{254}$ plate); IR (CCl$_4$) 2960, 2930, 2860, 1690, 1610, 1410, 1260, 1220, 1180 cm$^{-1}$; $^1$H-NMR (500 MHz, CDCl$_3$) δ: 7.92 (2H, d, J=8.3 Hz, C$_6$—H$_2$), 7.30 (2H, d, J=8.3 Hz, C$_6$—H$_2$), 3,59 (2H, t, J=7.4 Hz, BrCH$_2$), 3.22 (2H, t, J=7.4 Hz, Ph—CH$_2$), 2.94 (2H, t, J=7.4 Hz, Ph—CH$_2$), 1.73 (2H, qui, J=7.4 Hz,CH$_2$), 1.38~1.27 (8H, CH$_2$X4), 0.88 (3H, t, J=7.1 Hz, CH$_3$); EIMS m/z: 312 and 310 (M)$^+$, 228 and 226, 213 and 211, 20 203, 133, 104.

Step J-4: Preparation of diethyl acetamide-2-(4-octanoyl phenyl)ethyl malonate (6)

The fraction which contains 4-(2-bromoethyl) octanophenone prepared in the step N (500 mg) was dissolved in anhydrous ethanol (2 ml) to obtain a solution. Sodium ethylate (164 mg) was added to the solution. The mixture was stirred under atmosphere of nitrogen at 60° C. for 1 hour. The suspension was dissolved in N,N-dimethylformamide (10 ml) to obtain a solution. Diethyl acetamide malonate (1050 mg) and sodium ethylate (245 mg) were added to the solution, and the solution was stirred under atmosphere of nitrogen at 60° C. overnight. The reaction solution was poured into ice water, extracted with ether, and washed with saturated saline solution. The extracted solution was dried over anhydrous magnesium sulfate, and concentrated. The residue was subjected to silica gel column chromatography using hexane-ethyl acetate (1:0e3:1) as an eluate to obtain diethyl acetamide-2-(4-octanoyl phenyl)ethyl malonate (477 mg) in the form of colorless crystal.

Industrial Applicability

As has been discussed above in detail, the method for preparing 2-amino-1,3-propanediol derivatives according to the present invention permits the production of 2-amino-1,3-propanediol derivatives in high yield readily. The method for preparing 2-amino malonic acid derivatives according to the present invention permits the production of compound which is useful as an intermediate for preparing 2-amino-1,3-propanediol derivatives.

What is claimed is:

1. A process for preparing 2-amino malonic acid derivatives of formula (1):

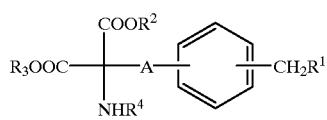

(1)

wherein A is linear or branched chain alkylene having from 1 to 10 carbon atoms, R$^1$ is linear or branched chain alkyl having from 2 to 20 carbon atoms, R$^2$ and R$^3$ are the same or different, and are lower alkyl or aralkyl, and R$^4$ is a protecting group, which process comprises the step of reducing a compound of formula (6):

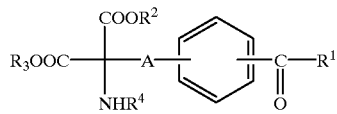

(6)

wherein A is linear or branched chain alkylene having from 1 to 10 carbon atoms, R$^1$ is linear or branched chain alkyl having from 2 to 20 carbon atoms, R$^2$ and R$^3$ are the same or different, and are lower alkyl or aralkyl, and R$^4$ is a protecting group.

2. A process for preparing a compound of the formula (6):

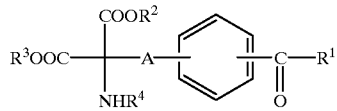

(6)

wherein

A is a linear or branched chain alkylene having from 1 to 10 carbon atoms,

R$^1$ is a linear or branched chain alkyl having from 2 to 20 carbon atoms,

R$^2$ and R$^3$ are the same or different, and are lower alkyl or aralkyl, and

R$^4$ is a protecting group, comprising:

reacting a compound of the formula (7) and 2-(N-substituted)amino malonic acid diester of the formula (3):

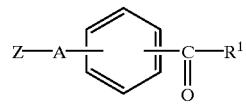

(7)

wherein

A is a linear or branched chain alkylene having from 1 to 10 carbon atoms,

R$^1$ is a linear or branched chain alkyl having from 2 to 20 carbon atoms, and

Z is a leaving group,

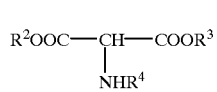

(3)

wherein

R$^2$ and R$^3$ are the same or different, and are lower alkyl or aralkyl, and

R$^4$ is a protecting group.

3. A process for preparing 2-amino malonic acid derivatives of the formula (1):

(1)

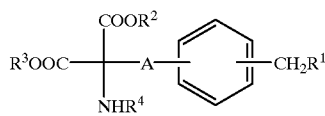

wherein

A is a linear or branched chain alkylene having from 1 to 10 carbon atoms, $R^1$ is a linear or branched chain alkyl having from 2 to 20 carbon atoms, $R^2$ and $R^3$ are the same or different, and are lower alkyl or aralkyl, and $R^4$ is a protecting group, comprising:

reacting a compound of the formula (7) and 2-(N-substituted)amino malonic acid diester of the formula (3) to obtain a compound of the formula (6):

(7)

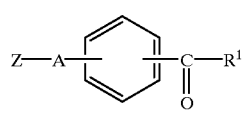

wherein

A is a linear or branched chain alkylene having from 1 to 10 carbon atoms, $R^1$ is a linear or branched chain alkyl having from 2 to 20 carbon atoms, and Z is a leaving group, (3)

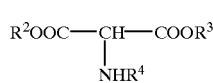

wherein $R^2$ and $R^3$ are the same or different, and are lower alkyl or aralkyl, and $R^4$ is a protecting group, (6)

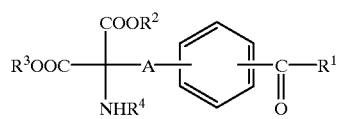

wherein

A is a linear or branched chain alkylene having from 1 to 10 carbon atoms, $R^1$ is a linear or branched chain alkyl having from 2 to 20 carbon atoms, $R^2$ and $R^3$ are the same or different, and are lower alkyl or aralkyl, and $R^4$ is a protecting group, and reducing the compound of the formula (6).

4. A process for preparing a compound of the formula (6):

(6)

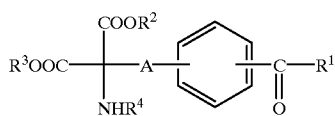

wherein

A is a linear or branched chain alkylene having from 1 to 10 carbon atoms, $R^1$ is a linear or branched chain alkyl having from 2 to 20 carbon atoms, $R^2$ and $R^3$ are the same or different, and are lower alkyl or aralkyl, and $R^4$ is a protecting group, comprising:

converting a hydroxyl group of a compound of the formula (5) to a leaving group to obtain a compound of a formula (7):

(5)

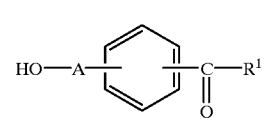

wherein

A is a linear or branched chain alkylene having from 1 to 10 carbon atoms, and $R^1$ is a linear or branched chain alkyl having from 2 to 20 carbon atoms, (7)

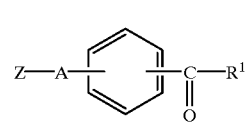

wherein

A is a linear or branched chain alkylene having from 1 to 10 carbon atoms, $R^1$ is a linear or branched chain alkyl having from 2 to 20 carbon atoms, and Z is a leaving group, and reacting the compound of the formula (7) and 2-(N-substituted)amino malonic acid diester of the formula (3):

(3)

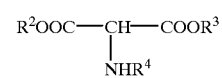

wherein $R^2$ and $R^3$ are the same or different, and are lower alkyl or aralkyl, and $R^4$ is a protecting group.

5. A process for preparing a compound of the formula (6):

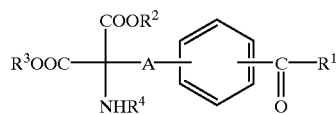
(6)

wherein
A is a linear or branched chain alkylene having from 1 to 10 carbon atoms,
$R^1$ is a linear or branched chain alkyl having from 2 to 20 carbon atoms,
$R^2$ and $R^3$ are the same or different, and are lower alkyl or aralkyl, and
$R^4$ is a protecting group, comprising:
deacylating a compound of the formula (9) to obtain a compound of the formula (5):

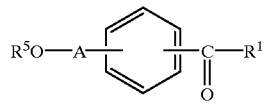
(9)

wherein
A is a linear or branched chain alkylene having from 1 to 10 carbon atoms,
$R^1$ is a linear or branched chain alkyl having from 2 to 20 carbon atoms, and
$R^5$ is an acyl type protecting group,

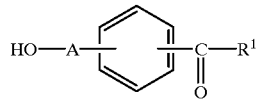
(5)

wherein
A is a linear or branched chain alkylene having from 1 to 10 carbon atoms, and
$R^1$ is a linear or branched chain alkyl having from 2 to 20 carbon atoms,
converting the hydroxyl group of the compound of the formula (5) to a leaving group to obtain the compound of the formula (7):

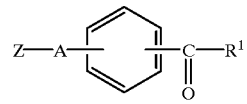
(7)

wherein
A is a linear or branched chain alkylene having from 1 to 10 carbon atoms,
$R^1$ is a linear or branched chain alkyl having from 2 to 20 carbon atoms, and
Z is a leaving group, and
reacting the compound of the formula (7) and 2-(N-substituted)amino malonic acid diester of the formula (3):

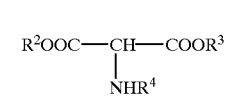
(3)

wherein
$R^2$ and $R^3$ are the same or different, and are lower alkyl or aralkyl, and
$R^4$ is a protecting group.

6. A process for preparing a compound of the formula (6):

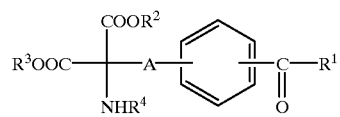
(6)

wherein
A is a linear or branched chain alkylene having from 1 to 10 carbon atoms,
$R^1$ is a linear or branched chain alkyl having from 2 to 20 carbon atoms,
$R^2$ and $R^3$ are the same or different, and are lower alkyl or aralkyl, and
$R^4$ is a protecting group, comprising:
reacting a compound of the formula (11) and a compound of the formula (15) to obtain a compound of the formula (7):

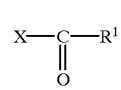
(11)

wherein
$R^1$ is a linear or branched chain alkyl having from 2 to 20 carbon atoms, and
X is a halogen,

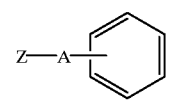
(15)

wherein
A is a linear or branched alkylene having from 1 to 10 carbon atoms, and
Z is a leaving group,

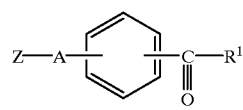
(7)

wherein
A is a linear or branched chain alkylene having from 1 to 10 carbon atoms,
$R^1$ is a linear or branched chain alkyl having from 2 to 20 carbon atoms, and Z is a leaving group, and reacting the compound of the formula (7) and 2-(N-substituted)amino malonic acid diester of the formula (3):

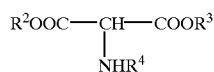
(3)

wherein
$R^2$ and $R^3$ are the same or different, and are lower alkyl or aralkyl, and
$R^4$ is a protecting group.

7. The process according to claim 1, wherein $R^2$ and $R^3$ are ethyl groups.
8. The process according to claim 2, wherein $R^2$ and $R^3$ are ethyl groups.
9. The process according to claim 3, wherein $R^2$ and $R^3$ are ethyl groups.
10. The process according to claim 4, wherein $R^2$ and $R^3$ are ethyl groups.
11. The process according to claim 5, wherein $R^2$ and $R^3$ are ethyl groups.
12. The process according to claim 6, wherein $R^2$ and $R^3$ are ethyl groups.
13. The process according to claim 1, wherein $R^4$ is an acetyl group.
14. The process according to claim 2, wherein $R^4$ is an acetyl group.
15. The process according to claim 3, wherein $R^4$ is an acetyl group.
16. The process according to claim 4, wherein $R^4$ is an acetyl group.
17. The process according to claim 5, wherein $R^4$ is an acetyl group.
18. The process according to claim 6, wherein $R^4$ is an acetyl group.
19. The process according to claim 1, wherein $R^1$ is an n-heptyl group.
20. The process according to claim 2, wherein $R^1$ is an n-heptyl group.
21. The process according to claim 3, wherein $R^1$ is an n-heptyl group.
22. The process according to claim 4, wherein $R^1$ is an n-heptyl group.
23. The process according to claim 5, wherein $R^1$ is an n-heptyl group.
24. The process according to claim 6, wherein $R^1$ is an n-heptyl group.
25. The process according to claim 1, wherein A is an ethylene group.
26. The process according to claim 2, wherein A is an ethylene group.
27. The process according to claim 3, wherein A is an ethylene group.
28. The process according to claim 4, wherein A is an ethylene group.
29. The process according to claim 5, wherein A is an ethylene group.
30. The process according to claim 6, wherein A is an ethylene group.
31. The process according to claim 2, wherein Z is chlorine, iodine, bromine, p-toluene sulfonyloxy, methane sulfonyloxy or trifluoromethane sulfonyloxy.
32. The process according to claim 3, wherein Z is chlorine iodine, bromine, p-toluene sulfonyloxy, methane sulfonyloxy or trifluoromethane sulfonyloxy.
33. The process according to claim 4, wherein Z is chlorine, iodine, bromine, p-toluene sulfonyloxy, methane sulfonyloxy or trifluoromethane sulfonyloxy.
34. The process according to claim 5, wherein Z is chlorine, iodine, bromine, p-toluene sulfonyloxy, methane sulfonyloxy or trifluoromethane sulfonyloxy.
35. The process according to claim 6, wherein Z is chlorine, iodine, bromine, p-toluene sulfonyloxy, methane-sulfonyloxy or trifluoromethane sulfonyloxy.
36. A process for preparing 2-amino-1,3-propanediol derivatives of the formula (17):

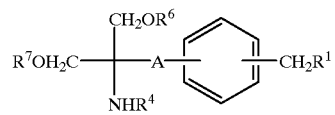
(17)

wherein
A is a linear or branched chain alkylene having from 1 to 10 carbon atoms,
$R^1$ is a linear or branched chain alkyl having from 2 to 20 carbon atoms, and
$R^4$, $R^6$ and $R^7$ are the same or different, and are hydrogen or protecting groups, comprising:
reducing a compound of the formula (19):

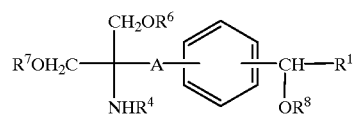
(19)

wherein
A is a linear or branched chain alkylene having from 1 to 10 carbon atoms,
$R^1$ is a linear or branched chain alkyl having from 2 to 20 carbon atoms, and
$R^4$, $R^6$, $R^7$ and $R^8$ are the same or different, and are hydrogen or protecting groups.

37. A process for preparing 2-amino-1,3-propanediol derivatives of the formula (17):

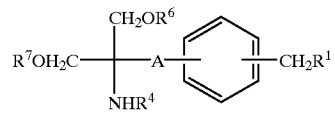
(17)

wherein
A is a linear or branched chain alkylene having from 1 to 10 carbon atoms,
$R^1$ is a linear or branched chain alkyl having from 2 to 20 carbon atoms, and
$R^4$, $R^6$ and $R^7$ are the same or different, and are hydrogen or protecting groups, comprising:
reducing a compound of the formula (6) and adding a protecting group, or deprotecting to obtain a compound of the formula (19):

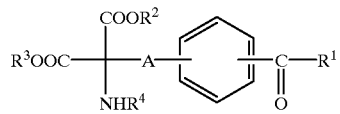

(6)

wherein
- A is a linear or branched chain alkylene having from 1 to 10 carbon atoms,
- $R^1$ is a linear or branched chain alkyl having from 2 to 20 carbon atoms,
- $R^2$ and $R^3$ are the same or different, and are lower alkyl or aralkyl, and
- $R^4$ is a protecting group,

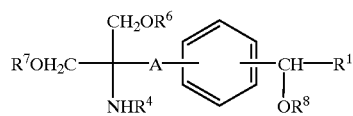

(19)

wherein
- A is a linear or branched chain alkylene having from 1 to 10 carbon atoms,
- $R^1$ is a linear or branched chain alkyl having from 2 to 20 carbon atoms, and
- $R^4$, $R^6$, $R^7$ and $R^8$ are the same or different, and are hydrogen or protecting groups, and reducing the compound of the formula (19).

38. A process for preparing 2-amino-1,3-propanediol-derivatives of the formula (17),

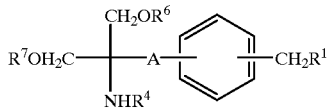

(17)

wherein
- A is a linear or branched chain alkylene having from 1 to 10 carbon atoms,
- $R^1$ is a linear or branched chain alkyl having from 2 to 20 carbon atoms, and
- $R^4$, $R^6$ and $R^7$ are the same or different, and are hydrogen or a protecting group, comprising:
  reacting the compound of the formula (7) and 2-(N-substituted)amino malonic acid diester of the formula (3) to obtain a compound of the formula (6),

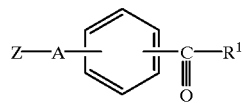

(7)

wherein
- A is a linear or branched chain alkylene having from 1 to 10 carbon atoms,
- $R^1$ is a linear or branched chain alkyl having from 2 to 20 carbon atoms, and Z is a leaving group,

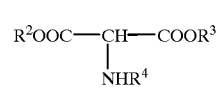

(3)

wherein
- $R^2$ and $R^3$ are the same or different, and are lower alkyl or aralkyl, and
- $R^4$ is a protecting group,

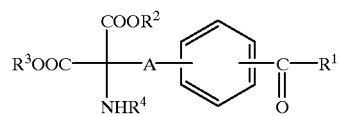

(6)

wherein
- A is a linear or branched chain alkylene having from 1 to 10 carbon atoms,
- $R^1$ is a linear or branched chain alkyl having from 2 to 20 carbon atoms,
- $R^2$ and $R^3$ are the same or different, and are lower alkyl or aralkyl, and
- $R^4$ is a protecting group,
- reducing the compound of the formula (6) and adding a protecting group, or deprotecting to obtain a compound of the formula (19):

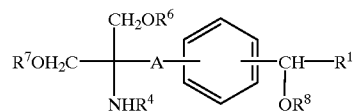

(19)

wherein
- A is a linear or branched chain alkylene having from 1 to 10 carbon atoms,
- $R^1$ is a linear or branched chain alkyl having from 2 to 20 carbon atoms, and
- $R^4$, $R^6$, $R^7$ and $R^8$ are the same or different, and are hydrogen or protecting groups, and reducing the compound of the formula (19).

39. The process according to claim 36, wherein $R^4$, $R^6$, $R^7$ and $R^8$ are acetyl groups or hydrogen.

40. The process according to claim 37, wherein $R^4$, $R^6$, $R^7$, and $R^8$ are acetyl groups or hydrogen.

41. The process according to claim 38, wherein $R^4$, $R^6$, $R^7$ and $R^8$ are acetyl groups or hydrogen.

42. The process according to claim 36, wherein $R^1$ is an n-heptyl group.

43. The process according to claim 37, wherein $R^1$ is an n-heptyl group.

44. The process according to claim 38, wherein $R^1$ is an n-heptyl group.

45. The process according to claim 36, wherein A is an ethylene group.

46. The process according to claim 37, wherein A is an ethylene group.

47. The process according to claim 38, wherein A is an ethylene group.

* * * * *